United States Patent [19]

Tsushima et al.

[11] 4,286,088
[45] Aug. 25, 1981

[54] PROCESS FOR PREPARING 7-AMINOCEPHALOSPORINS

[75] Inventors: Susumu Tsushima; Norichika Matsumoto, both of Osaka; Masayasu Kato, Ashiya, all of Japan

[73] Assignee: Takeda Chemical Industries, Ltd., Osaka, Japan

[21] Appl. No.: 966,654

[22] Filed: Dec. 5, 1978

[30] Foreign Application Priority Data

Dec. 12, 1977 [JP] Japan .................. 52/149718
Dec. 14, 1977 [JP] Japan .................. 52/151105

[51] Int. Cl.$^3$ .......................................... C07D 501/04
[52] U.S. Cl. ........................................ 544/16; 544/26; 544/30; 424/246
[58] Field of Search ............... 544/30, 19, 22, 26, 544/16, 27, 21

[56] References Cited

U.S. PATENT DOCUMENTS

| | | | |
|---|---|---|---|
| 3,839,328 | 10/1974 | Chauvette | 544/30 |
| 3,931,161 | 1/1976 | Buitar et al. | 544/19 |
| 3,932,392 | 1/1976 | Johnson et al. | 544/19 |
| 4,036,833 | 1/1977 | Ishimaru et al. | 544/19 |

FOREIGN PATENT DOCUMENTS 1239814 7/1971 United Kingdom ................. 260/243 C

*Primary Examiner*—Nicholas S. Rizzo
*Attorney, Agent, or Firm*—Craig and Antonelli

[57] ABSTRACT

7-Aminocephalosporin of the formula:

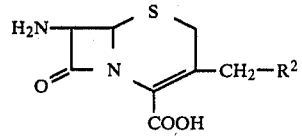

wherein $R^2$ is 3-oxobutyryloxy group, 1-methyl-1H-tetrazol-5-ylthio group or 1-(2-dimethylaminoethyl)-1H-tetrazol-5-ylthio group, or its salt is prepared by first protecting the carboxyl group at 4-position of the compound of the formula:

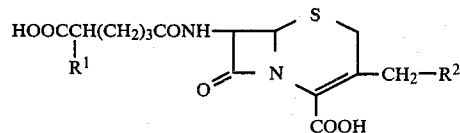

wherein $R^1$ is an amino group which may be protected and $R^2$ is the same as defined above, or its salt with an acetyl or propionyl halide, then cleaving the amide group at 7-position of said compound by converting the amide bond to an imino halide, then to an imino ether and subjecting the imino ether to solvolysis.

11 Claims, No Drawings

PROCESS FOR PREPARING 7-AMINOCEPHALOSPORINS

This invention relates to a process for preparing 7-aminocephalosporins, which comprises cleaving the amide group at 7-position of a compound represented by the following formula or its salt:

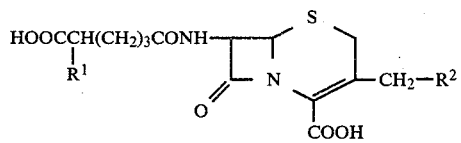

wherein $R^1$ stands for an amino group which may be protected, and $R^2$ stands for 3-oxobutyryloxy group, 1-methyl-1H-tetrazol-5-ylthio group or 1-(2-dimethylaminoethyl)-1H-tetrazol-5-ylthio group, to produce a compound represented by the following formula or its salt:

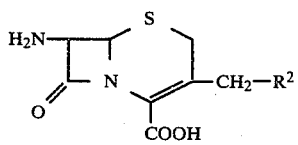

wherein $R^2$ is the same as defined above.

In case when $R^2$ in the above formula (II) is 1-methyl-1H-tetrazol-5-ylthio group, the compound (II) is 7β-amino-3-[[(1-methyl-1H-tetrazol-5-yl)thio]methyl]ceph-3-em-4-carboxylic acid (hereinafter abbreviated as 7-ATC); while, when $R^2$ is 1-(2-dimethylaminoethyl)-1H-tetrazol-5-ylthio group, it is 7β-amino-3-[[[1-(2-dimethylaminoethyl)-1H-tetrazol-5-yl]thio]methyl]ceph-3-em-4-carboxylic acid (hereinafter abbreviated as 7-AMTC); and, when $R^2$ is 3-oxobutyryloxy group, it is 7β-amino-3-(3-oxobutyryloxymethyl)ceph-3-em-4-carboxylic acid (hereinafter abbreviated as 7-AOC).

The most conventional method in the art for cleaving acylamino group at 7-position of cephalosporins is disclosed in Japanese published examined patent application No. 13862/1966 (corresponding to British Pat. No. 1041985, U.S. Pat. No. 3,875,151 and Dutch Pat. No. 640142). That is, the amide bond is converted to an imino halide, which is further converted to an imino ether, and the resultant imino ether is subjected to hydrolysis to form an amino group.

This method, however, cannot be practiced without previous protection of the carboxyl group at 4-position. As protective groups mentioned in the aforesaid patent, there are benzyl group and benzhydryl group. Such protective groups are required to be eliminated for restoration of the carboxyl group. Elimination of these groups is required to be conducted under strong conditions such as by the use of trifluoroacetic acid and anisole or catalytic reduction, whereby cleavage of β-lactam ring is accompanied to result in poor yield of the subject compound.

As the result of extensive studies, it has now been found that the compound (II) can be prepared from the compound (I) with good yield when the carboxyl group at 4-position of the compound (I) is protected by acetyl or propionyl halide such as acetyl chloride or propionyl chloride. The present invention is accomplished based on such a finding.

The starting compound (I) to be used in this reaction can be obtained according to the method as described in German Laid-open Specification No. 2607064 (corresponding to Belgian Pat. No. 838833) or methods similar thereto. The compound (I) may be used in the free form or in the salt form with an alkali or alkaline earth metal such as sodium, potassium, calcium, lithium and the like; a basic amino acid such as lysine, arginine, ornithine, histidine and the like; organic amine such as pyridine, picoline, N-methylmorpholine, quinoline, isoquinoline, N,N-dimethylaniline, triethylamine and the like; a polyhydroxy alkylamine such as N-methyl gulcamine, di-ethanolamine, tri-ethanolamine, tris-hydroxy methylaminomethane and the like; or an acid such as hydrochloric acid, sulfuric acid, trifluoroacetic acid and the like. In the above compound (I), $R^1$ represents an amino group which may be protected before protecting the carboxyl group at 4-position. As protective groups, there may be used those conventionally used in peptide chemistry and all protective groups for amino groups at 6- or 7-acyl groups of penicillins or cephalosporins are applicable here. Since it is not required to eliminate the protective group in the process of the present invention, there may also be employed groups of which elimination is difficult or impossible, for example, acrylamino groups. The acyl groups in said acylamino groups frequently used may include phthaloyl, benzoyl, p-nitrobenzoyl, toluoyl, naphthoyl, p-tert-butylbenzoyl and so on. The starting compound (I) thus prepared may also be provided for use as it is, without specific isolation or purification, in the reaction for preparation of the compound (II).

The compound (II) can be prepared from the compound (I) according to the following procedures. First, the compound (I) is allowed to react with an acetyl or propionyl halide such as acetyl chloride or propionyl chloride to protect the carboxyl group at 4-position. This reaction may advantageously be carried out in an inert solvent such as dichloromethane, chloroform, 1,2-dichloroethane or tetrahydrofuran, under anhydrous conditions, in the presence of a tertiary amine such as trimethyl amine, triethyl amine, quinoline, pyridine, N,N-dimethyl aniline, N,N-diethyl aniline, N-methyl morpholine. The compound (I) is dissolved in the solvent after formation of salt with these amines. This protection reaction may be conducted at −50° C. or higher, but side reactions will occur at around room temperature to give no product with high purity. Thus, it is preferred to conduct the reaction at −50° C. to 0° C., particularly at −10° C. to −50° C. Since the carboxyl group in the acylamino group at 7-position is protected by acetyl halide as well as one at 4-position, the protective agent is added in an amount of at least twice, preferably 8–12 times as much as moles of the compound to be protected in order to obtain favorable results.

Then, the reaction product as prepared above is allowed to react with an imino halide-forming agent, e.g. phosphorous pentachloride, etc., to be converted to an imino halide. This reaction may preferably be carried out in an inert solvent as mentioned above in the presence of a tertiary amine such as N,N-dimethyl aniline, N,N-diethyl aniline, etc. The reaction temperature is not specifically limited but preferably in the range from −55° C. to 0° C. To the thus prepared imino halide is added a lower alkanol such as methanol, ethanol, n- propanol, n-butanol, iso-butanol and the like for conversion to an imino ether. These reactions may be conducted by conventional techniques.

The thus prepared imino ether is subjected to solvolysis with water, lower alkanols as mentioned above or others. For example, water is added to the reaction mixture to effect hydrolysis, followed by isolation purification according to conventional method such as precipitation of the objective compound by adjusting pH of the reaction mixture to around isoelectric point of the product (II) or removal of the solvent.

The free compound (II) and its salt as set forth in connection with the compound (I) are important intermediates for preparation of antimicrobial substances. For example, as disclosed in U.S. Pat. No. 4,080,498 (corresponding to British Pat. No. 1491081, Belgian Pat. No. 823861 and South African Pat. No. 7418050), Japanese patent application No. 37374/1976 (corresponding to German Laid-open Specification 2714419) and Japanese patent application No. 104583/1976 (corresponding to German Laid-open specification 2738711), 7β-[2-(2-aminothiazol-4-yl)acetamido]-3-[[[1-(2-dimethylaminoethyl)-1H-tetrazol-5-yl]thio]methyl]ceph-3-em-4-carboxylic acid and 7β-[2-(2-aminothiazol-4-yl)acetamido]-3-[[(1-methyl-1H-tetrazol-5-yl)thio]methyl]ceph-3-em-4-carboxylic acid which are prepared by reacting 7-AMTC and 7-ATC, respectively, with 4-halogeno-3-oxobutyryl-halogenide to be converted to 7β-(4-halogeno-3-oxobutyrylamino) derivatives and then reacting them with thiourea, are known to exhibit excellent antimicrobial activities. Furthermore, 3-(4-carbamoyl-1-pyridiniomethyl)-7β-(D-α-sulfophenylacetamido)-ceph-3-em-4-carboxylate monosodium salt obtained by reacting 7-AOC and D-α-sulfophenyl acetyl chloride, and then with iso-nicotinic acid amide, as disclosed by Japanese patent application No. 83869/1977 (corresponding to German Laid-open Specification No. 2607064), is a compound having strong antimicrobial activity against Pseudomonas.

EXAMPLE 1

7β-(D-5-carboxy-5-phthalimidovaleramido)-3-hydroxymethylceph-3-em-4-carboxylic acid di-triethylamine salt (8.25 g) is dissolved in dichloromethane (120 ml.). To the resultant solution are added triethylamine (2.3 ml.) and diketone (3.0 ml.), and the mixture is stirred at 20° C. for one hour. The reaction mixture is cooled to −20° C., mixed with acetyl chloride (11.5 ml.) and thereafter stirred at −10° C. to 0° C. for 20 minutes. N,N-dimethyl aniline (19 ml.) is added to the resultant reaction mixture and the mixture is cooled to −50° C., followed by stirring for 20 minutes with addition of phosphorous pentachloride (12.0 g). Methanol (50 ml.) is added to the reaction mixture at not higher than −30° C., followed by stirring at −20° C. to −15° C. for 20 minutes, and the mixture is further vigorously agitated with addition of water (100 ml.) for 5 minutes. After the mixture is left to stand, the aqueous layer is separated. The aqueous solution is mixed with methanol (55 ml.) and adjusted under stirring with a saturated aqueous potassium carbonate solution at room temperature to pH 3.4. After stirring the solution under ice-cooling for 30 minutes, the precipitated crystals are collected by filtration, washed with water and acetone successively and dried to give 7β-amino-3-(3-oxobutyryloxymethyl) ceph-3-em-4-carboxylic acid. Yield: 4.46 g.

IR(KBr): cm⁻¹ 3200, 1800, 1745, 1720, 1622; NMR (D₂O+NaOD)δ: 2.27(3H,s), 3.48(2H,ABq,J=18Hz), 4.6-5.6(4H,m).

EXAMPLE 2

7β-[D-5-(p-t-butylbenzamido)-5-carboxyvaleramido]-3-hydroxymethylceph-3-em-4-carboxylic acid ditriethylamine salt (6.55 g) is suspended in dichloromethane (60 ml.). The resultant suspension is mixed with triethylamine (1.1 ml.) and diketone (1.5 ml.), and stirred for 60 minutes. Then, cooling the reaction mixture to −50° C. and adding acetyl chloride (7.6 ml.) and N,N-dimethyl aniline (9.5 ml.) successively thereto, the mixture is stirred at −45° C. to −40° C. for 30 minutes. The reaction mixture is subsequently mixed with phosphorous pentachloride (6.0 g) at −50° C., followed by stirring at −45° C. to −40° C. for 25 minutes, and methanol (25 ml.) is added dropwise slowly thereto. During addition of the methanol, the inner temperature is maintained at not higher than −30° C. Then, water (50 ml.) is added to the reaction mixture and, after stirring the mixture vigorously at −5° C. to 0° C. for 5 minutes, the aqueous layer is separated. The organic layer is further subjected to extraction with water (5 ml.). The aqueous layers are combined, mixed with methanol (25 ml.) and adjusted under stirring with 40% aqueous potassium carbonate solution to pH 3.4. After cooling the mixture at 0° C. to 5° C. for 30 minutes, the precipitates are collected by filtration and washed with water and acetone successively, followed by drying, to give 7β-amino-3-(3-oxobutyryloxymethyl)ceph-3-em-4-carboxylic acid. Yield: 2.21 g. The IR spectrum of this product is substantially identical with that obtained in Example 1.

EXAMPLE 3

When the reactions as described in Example 1 are repeated by using propionyl chloride (14 ml.) in place of acetyl chloride, there is obtained 7β-amino-3-(3-oxobutyryloxymethyl)ceph-3-em-4-carboxylic acid. Yield: 4.31 g. The IR spectrum of this product is substantially identical with that obtained in Example 1.

EXAMPLE 4

7β-(D-5-carboxy-5-phthalimidovaleramido)-3-[[[1-(2-dimethylaminoethyl)-1H-tetrazol-5-yl]thio]methyl]-ceph-3-em-4-carboxylic acid hydrochloride (34.8 g) *1 (purity=75%) is suspended in dichloromethane (700 ml.) and dissolved at not higher than 5° C. with addition of triethyl amine (17.9 ml.). This reaction mixture is cooled to −45° C., mixed with N,N-dimethyl aniline (66 g) and then with acetyl chloride (44 g), followed by stirring at −45° C. to −40° C. for 30 minutes. Then, after adding phosphorous pentachloride (42 g) of the mixture, the reaction is carried out at −45° C. to −40° C. for 30 minutes. After the reaction, iso-butanol (170 ml.) is added dropwise to the reaction mixture at not higher than −30° C. After stirring the mixture at −35° C. to −30° C. for 60 minutes, water (300 ml.) is added thereto, followed further by stirring at −5° C. for 5 minutes. The aqueous layer is separated, washed with dichloromethane (100 ml.), mixed with ethyl acetate (100 ml.) under stirring and adjusted to pH 6.0 with triethyl amine. The aqueous layer is separated, adjusted to pH 3.2 with 4 N-HCl, then concentrated under reduced pressure and poured into ethanol (1 liter). After stirring the precipitates at not higher than 5° C. for 30 minutes, they are collected by filtration, washed with ethanol and acetone successively and dried under reduced pressure to give 7β-amino-3-[[[1-(2-dimethylaminoethyl)-1H-tetrazol-5-yl]thio]methyl]ceph-3-em-4-carboxylic acid (7-AMTC) mono-hydrochloride. Yield: 16.6 g, *2 Purity=81.5%, Yield percentage: 85%.

(*1) Measurement of purity of the starting materials: by high speed liquid chromatography; Apparatus: Hitachi 634-B model; Column: Hitachi 2614-cation exchange resin 50 cm; Temperature: 50° C.; Eluant: citrate buffer, pH 6.00; Column pressure: 33 kg/cm².

(*2) Measurement of purity of 7-AMTC: by high speed liquid chromatography; Apparatus: Hitachi 634-B model; Column: Hitachi 2614-cation exchange resin 50 cm; Temperature: 50° C.; Eluant: citrate buffer, pH 5.00; Elution speed: 0.32 ml./minute.

IR(KBr): cm$^{-1}$ 1780, 1615; NMR($D_2O$): 3.11(6H,s), 3.83(2H,ABq,J=18Hz), 3.90(2H,t,J=6Hz), 4.27(2H,ABq,J=18Hz), 4.97(2H,t,J=6Hz), 5.16(1H,d,J=5Hz), 5.33(1H,d,J=5Hz).

EXAMPLE 5

According to the same procedures as described in Example 4 except that propionyl chloride (51 g) is used in place of acetyl chloride, 7-AMTC-mono-hydrochloride is prepared. The IR and NMR spectra of this product are substantially identical with those of the product obtained in Example 4. Yield: 16.6 g, *2 Purity: 89.0%, Yield percentage: 86%.

(*2) Measurement of purity of 7-AMTC: by high speed liquid chromatography; Apparatus: Hitachi 634-B model; Column: Hitachi 2614-cation exchange resin 50 cm; Temperature: 50° C.; Eluant: citrate buffer, pH 5.00; Elution speed: 0.32 ml./minute.

EXAMPLE 6

According to the same procedures as described in Example 4 except that the amount of acetyl chloride added is changed from 44 g to 34 g and subsequent stirring is effected at −10° C. to −5° C. for 20 minutes, 7-AMTC-mono-hydrochloride is prepared. Yield: 16.2 g, *2 Purity: 80.2%, Yield percentage: 82%.

(*2) Measurement of purity of 7-AMTC: by high speed liquid chromatography; Apparatus: Hitachi 634-B model; Column: Hitachi 2614-cation exchange resin 50 cm; Temperature: 50° C.; Eluant: citrate buffer, pH 5.00; Elution speed: 0.32 ml./minute.

EXAMPLE 7

7β-(D-5-carboxy-5-phthalimidovaleramido)-3-[[[1-(2-dimethylaminoethyl)-1H-tetrazol-5-yl]thio]methyl]-ceph-3-em-4-carboxylic acid hydrochloride (34.8 g) *1 (purity=75%) is suspended in dichloromethane (700 ml.) and dissolved at not higher than 5° C. with addition of triethylamine (17.9 ml.). This reaction mixture is cooled to −30° C., mixed with N,N'-dimethyl aniline (68 g) and then with acetyl chloride (45 g), followed by stirring at −20° C. to −15° C. for 10 minutes. Then, the reaction mixture is cooled to −55° C. and phosphorous pentachloride (34 g) is added thereto. The reaction is carried out at −55° C. to −50° C. for 45 minutes. After the reaction, iso-butanol (170 ml.) is added dropwise to the reaction mixture, cooling is discontinued and the reaction mixture is warmed to room temperature. Stirring is continued at room temperature for 20 minutes and then at 0° C. for 30 minutes. The precipitated crystals are collected by filtration, washed with a small amount of dichloromethane and dried under reduced pressure to give 7β-amino-3-[[[1-(2-dimethylaminoethyl)-1H-tetrazol-5-yl]thio]methyl]ceph-3-em-4-carboxylic acid (7-AMTC) dihydrochloride (24.1 g).

(*1) Measurement of purity of the starting materials: by high speed liquid chromatography; Apparatus: Hitachi 634-B model; Column: Hitachi 2614-cation exchange resin 50 cm; Temperature: 50° C.; Eluant: citrate buffer, pH 6.00; Colum pressure: 33 kg/cm².

IR(KBr): cm$^{-1}$ 1780, 1715, 1625; NMR($D_2O$): δ 3.11(6H,s), 3.89(2H,t,J=6Hz), 3.90(2H,ABq,J=18Hz), 4.38(2H,ABq, J=13Hz), 5.00(2H,t,J=6Hz), 5.21(1H, d, J=5Hz), 5.38(1H,d,J=5Hz).

The thus prepared 7-AMTC dihydrochloride is dissolved in water (15 ml.) and methanol (45 ml.), admixed with acetonitrile (75 ml.) and then adjusted to pH 3.4 with triethyl amine, followed by addition of acetonitrile (750 ml.). After cooling the mixture to 0° C. and stirring the mixture for one hour, the precipitates are collected by filtration and washed with acetonitrile to give 7-AMTC-mono-hydrochloride. The IR and NMR spectra of this product are substantially identical with those of the product obtained in Example 4. Yield: 16.5 g, *2 Purity: 82.5%, Yield percentage: 86%.

(*2) Measurement of purity of 7-ATMTC: by high speed liquid chromatography; Apparatus: Hitachi 634-B Model; Column: Hitachi 2614-cation exchange resin 50 cm; Temperature: 50° C.; Eluant: citrate buffer, pH 5.00; Elution speed: 0.32 ml./minute.

EXAMPLE 8

In place of adding acetyl chloride and stirring the mixture at −20° C. to −15° C. for 10 minutes in Example 7, propionyl chloride (56 g) is added and the mixture is stirred at −20° C. to −15° C. for 10 minutes, following otherwise the same procedures as in Example 7, 7-AMTC mono-hydrochloride is obtained. Yield: 15.6 g; *2 Purity: 80%; Yield percentage: 84%. The IR(KBr) spectrum and NMR($D_2O$) spectrum of this product are substantially identical with absorption spectra of those of Example 4.

(*2) Measurement of purity of 7-AMTC: by high speed liquid chromatography; Apparatus: Hitachi 634-B model; Column: Hitachi 2614-cation exchange resin 50 cm; Temperature: 50° C.; Eluant: citrate buffer, pH 5.00; Elution speed: 0.32 ml./minute.

EXAMPLE 9

7β-(D-5-carboxy-5-phthalimidovaleramido)-3-[[(1-methyl-1H-tetrazol-5-yl)thio]methyl]ceph-3-em-4-carboxylic acid *3 (Purity=83%)(6.0 g) is suspended in dichloromethane (160 ml.) and dissolved with stirring under ice-cooling with addition of triethyl amine (3.0 ml.). The solution is cooled to −45° C. and stirred for 20 minutes with addition of N,N-dimethyl aniline (16 ml.) and acetyl chloride (9.2 ml.). The reaction mixture is cooled to −55° C. and stirred for 45 minutes with addition of phosphorous pentachloride (7.9 g). Then, methanol (30 ml.) is added dropwise to the mixture while controlling the temperature of the reaction mixture at not over −30° C., followed by addition of water (50 ml.). The mixture is adjusted to pH 3.3 with addition of an aqueous sodium carbonate solution and subjected to stirring under ice-cooling for 30 minutes. The precipitated crystals are collected by filtration and washed sucessively with water, acetone and dichloromethane, followed by drying, to give 7β-amino-3-[[(1-methyl-1H-tetrazol-5-yl)thio]methyl]ceph-3-em-4-carboxylic acid (7-ATC). Yield: 2.66 g; *4 Purity=86%; Yield percentage: 84%.

(*3) Measurement of purity of the starting material: by thin layer chromatography; Thin layer: Kieselgel GF 254, 0.25 mm, subjected to silicon impregnation treatment; Eluant: 0.001 M sodium acetate-ethanol mixture (10:1, V/V).

(*4) Measurement of purity of 7-ATC: by high speed liquid chromatography; Column: Hitachi 2614-cation exchange resin 50 cm; Temperature: 30° C.; Eluant: citrate buffer, pH 5.0; Elution speed: 0.1 ml./minute.

IRT(KBr): cm$^{-1}$ 1795; NMR($D_2O$+$NaHCO_3$): 3.61 and 3.98(2H,ABq,J=18 Hz), 4.21(3H,s), 5.21(1 H,d,J=4.5 Hz), 5.60(1 H,d,J=4.5 Hz).

EXAMPLE 10

7β-[D-5-(p-t-butylbenzamido)-5-carboxyvaleramido]-3-[[[1-(2-dimethylaminoethyl)-1H-tetrazol-5-yl]thio]methyl]ceph-3-em-4-carboxylic acid (17.5 g) *1 purity=78%) is suspended in dichloromethane (350 ml.) and admixed with triethylamine (8.9 ml.) at not higher than 5° C., followed by stirring at 0° C. to 5° C. for 30 minutes. The reaction mixture is cooled to −30° C., at which acetyl chloride is added dropwise thereto, and the mixture is then stirred at −25° C. to −20° C. for 20 minutes. After cooling the reaction mixture to −60° C., N,N-dimethyl aniline (33 g) and then phosphorous pentachloride (21 g) are added thereto, followed by stirring at −55° C. to −50° C. for 40 minutes. Subsequently, iso-butanol (85 ml.) is added dropwise at not higher than −30° C. to the mixture and the reaction is carried out at −35° C. to −30° C. for one hour. Finally, water (150 ml.) is added to the reaction mixture and the resultant mixture is subjected to vigorous agitation at −5° C. to 0° C. for 5 minutes. The aqueous layer is separated and the organic layer is further extracted with water (50 ml.). The aqueous layers are combined, washed with dichloromethane (50 ml.), adjusted to pH 6.0 with triethylamine and stirred with addition of ethyl acetate (100 ml.). The resultant aqueous layer is separated and the organic layer is further extracted with water (25 ml.). The aqueous layers are combined, adjusted to pH 3.2 with 4N-HCl and then concentrated under reduced pressure. The concentrate is then poured into ethanol (500 ml.) and, after stirring the mixture at 0° C. to 5° C. for 30 minutes, the precipitates are collected by filtration and washed with ethanol and then with acetone, followed by drying under reduced pressure, to give 7β-amino-3-[[[1-(2-dimethylaminoehyl)-1H-tetrazol-5-yl]thio]methyl]ceph-3-em-4-carboxylic acid mono-hydrochloride. The IR and NMR spectra of this product are substantially identical with those of the product obtained in Example 4. Yield: 8.2 g, *2 Purity: 81.0%, Yield percentage: 84%.

(*1) Measurement of purity of the starting materials: by high speed liquid chromatography; Apparatus: Hitachi 634-B model; Column: Hitachi 2614-cation exchange resin 50 cm; Temperature: 50° C.; Eluant: citrate buffer, pH 6.00; Column pressure: 33 kg/cm².

(*2) Measurement of purity of 7-AMTC: by high speed liquid chromatography; Apparatus: Hitachi 634-B model; Column: Hitachi 2614-cation exchange resin 50 cm; Temperature: 50° C; Eluant: citrate buffer, pH 5.00; Elution speed: 0.32 ml./minute.

What we claim is:

1. A process for preparing a compound of the formula:

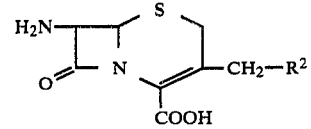

wherein $R^2$ is 3-oxobutyryloxy group, 1-methyl-1H-tetrazol-5-ylthio group or 1-(2-dimethylaminoethyl)-1H-tetrazol-5-ylthio group, or its salt which comprises reacting a compound of the formula:

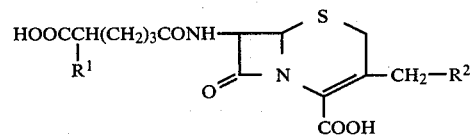

wherein $R^1$ is an amino group which may be protected and $R^2$ is the same as defined above or its salt with an acetyl or propionyl halide at −10° C. to −50° C., then with an imino halide-forming agent to be converted to an imino halide, which is further reacted with a lower alkanol to be converted to an imino ether, and subjecting the imino ether to solvolysis.

2. A process according to claim 1, wherein $R^2$ is 3-oxobutyryloxy group.

3. A process according to claim 1, wherein $R^2$ is 1-methyl-1H-tetrazol-5-ylthio group.

4. A process according to claim 1, wherein $R^2$ is 1-(2-dimethylaminoethyl)-1H-tetrazol-5-ylthio group.

5. A process according to claim 1, wherein $R^1$ is an acylamino group.

6. A process according to claim 5, wherein the acyl in the acylamino group is phthaloyl, benzoyl, p-nitrobenzoyl, toluoyl, naphthoyl or p-tert-butylbenzoyl group.

7. A process according to claim 1, wherein the reaction with an acetyl or propionyl halide is carried out in an inert solvent in the presence of a tertiary amine.

8. A process according to claim 1, wherein the reaction with an acetyl or propionyl halide is carried out by the addition of the halide in an amount of at least twice the molar amount required to react with the carboxyl group at the 4-position.

9. A process according to claim 1, wherein the reaction with an acetyl or propionyl halide is carried out by the addition of the halide in an amount of from 8 to 12 times the molar amount required to react with the carboxyl group at the 4-position, whereby the carboxyl group in the acetyl amino group at the 7-position as well as the carboxyl group at the 4-position are protected.

10. A process according to claim 1, wherein the reaction with the imino halide-forming agent is carried out in an inert organic solvent in a presence of a tertiary amine at from −55° C. to 0° C.

11. A process according to claim 1, wherein the imino halide-forming agent is phosphorus pentachloride.

* * * * *